US00PP12767P2

(12) United States Plant Patent
Pinney, Jr.

(10) Patent No.: US PP12,767 P2
(45) Date of Patent: Jul. 9, 2002

(54) BIRCH TREE NAMED 'UENCI'

(75) Inventor: Thomas S. Pinney, Jr., Sturgeon Bay, WI (US)

(73) Assignee: Evergreen Nursery Company, Inc., Sturgeon Bay, WI (US)

( * ) Notice: Subject to any disclaimer, the term of this patent is extended or adjusted under 35 U.S.C. 154(b) by 0 days.

(21) Appl. No.: 09/395,056

(22) Filed: Sep. 13, 1999

(51) Int. Cl.[7] ..... A01H 5/00

(52) U.S. Cl. ..... Plt./216
(58) Field of Search ..... Plt./216

*Primary Examiner*—Bruce R. Campell
*Assistant Examiner*—Susan B. McCormick
(74) *Attorney, Agent, or Firm*—W. Dennis Drehkoff; Ladas & Parry

(57) ABSTRACT

A new and distinct cultivar of *Betula papyrifera* named 'Uenci' characterized by its narrow, open, vigorous and upright growth habit, fast growth rate; semi-exfoliating bark when mature and very high tolerance to the Bronze Birch Borer.

4 Drawing Sheets

The present invention comprises a new and distinct cultivar of a birch tree, botanically known as *Betula papyrifera*, and is hereto referred to by the cultivar name "Uenci".

BACKGROUND OF THE INVENTION

'Uenci' was discovered by the inventor in a group *Betula payrifera* in a provenance test plot planted in Wooster, Ohio, in 1986. 'Uenci' was originated from the open pollinated cross in a birch selection/breeding program on Evergreen Nursery Company, Inc., property in Sturgeon Bay, Wis. The female parent was *Betula papyrifera.* The pollen parent was *Betula papyrifera.* 'Uenci' was first noticed with a narrow, open, vigorous, upright growth habit, white semi-exfoliating bark and a very high resistance to the Bronze Birch Borer. The upright and open growth of the crown facilitates clumping of the trees. The open growth further allows for grass to grow under the tree since more sunlight can penetrate the ground. The cultivar has been asexually reproduced in Sturgeon Bay, Wis. The current propagation is by micropropation at Sturgeon Bay, Wis. Horticultural examination of selected units has demonstrated that the combination of characteristics as herein disclosed for 'Uenci' are firmly fixed and retained through its successive generations of asexual reproduction. 'Uenci' has been observed in Sturgeon Bay, Wis. and Wooster, Ohio, since 1986 and characteristics have been stably maintained. The cultivar reproduces true to type. The new cultivar has not been observed under all possible environmental conditions. The phenotype may vary somewhat with variations in environment such as temperature, day length and light intensity, without a change in the genotype of the cultivar. The following observations, measurements, and comparisons describe the plants grown in Sturgeon Bay, Wis. under natural field conditions which approximate those generally used in commercial growing operations.

SUMMARY OF THE INVENTION

The following traits have been repeatedly observed and are determined to be basic characterisitcs of 'Uenci' which in combination distinguish this birch tree as a new and distinct cultivar:

1. Distinctive narrow, open, vigorous, upright growth habit with branching angles about 50°.

2. Bark color changes as the tree matures; from brown turning to white.
3. Semi-exfoliating bark when mature.
4. Very high resistance to the Bronze Birch Borer.
5. Fast growth rate.

The new cultivar can be compared to the nonpatented *Batula papyrifera* for the foregoing characteristics differ from the nonpatented variety in that the nonpatented variety has variable resistance to the Bronze Birch Borer, has a loose oval growth habit and its bark is exfoliating.

BRIEF DESCRIPTION OF THE DRAWINGS

The accompanying color photographs show typical characteristics of 'Uenci', with colors being as true as possible with illustration of this type.

DETAILED BOTANICAL DESCRIPTION

Figure 1:
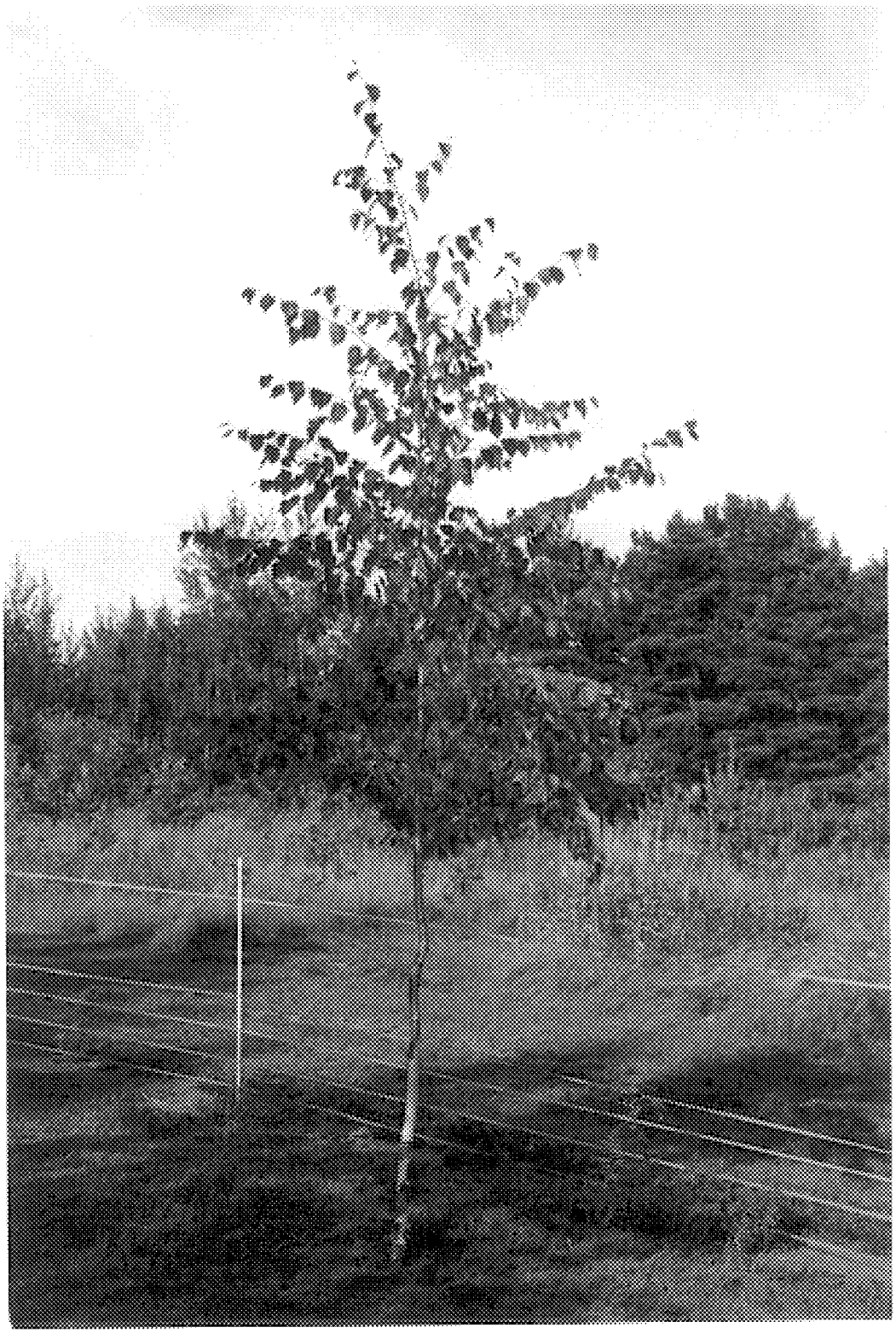
FIG. 1 is the side view of a specimen of 'Uenci' showing the narrow open growth habit.
Figure 2:
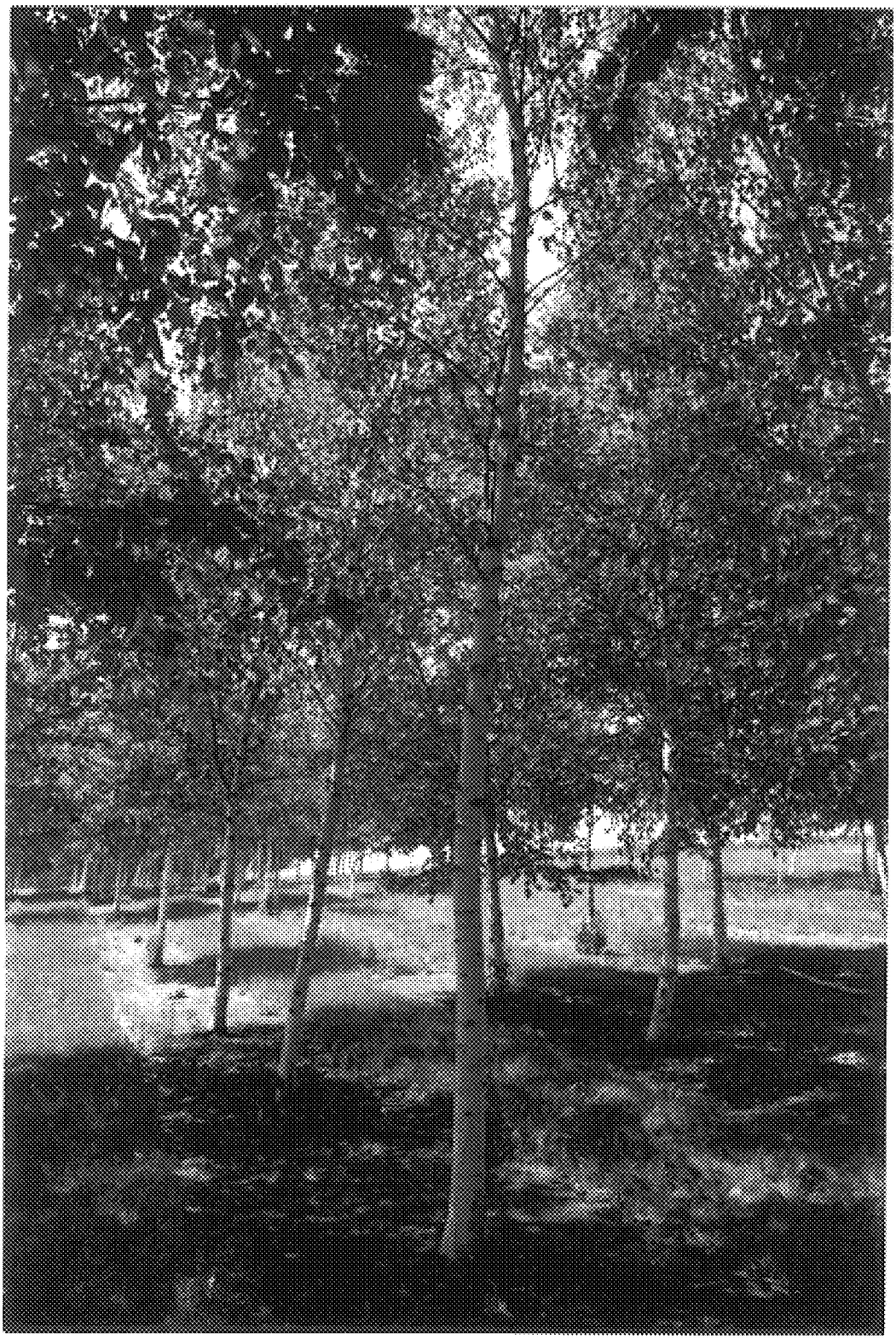
FIG. 2 is the side view of the original tree of the 'Uenci' cultivar.
Figure 3:
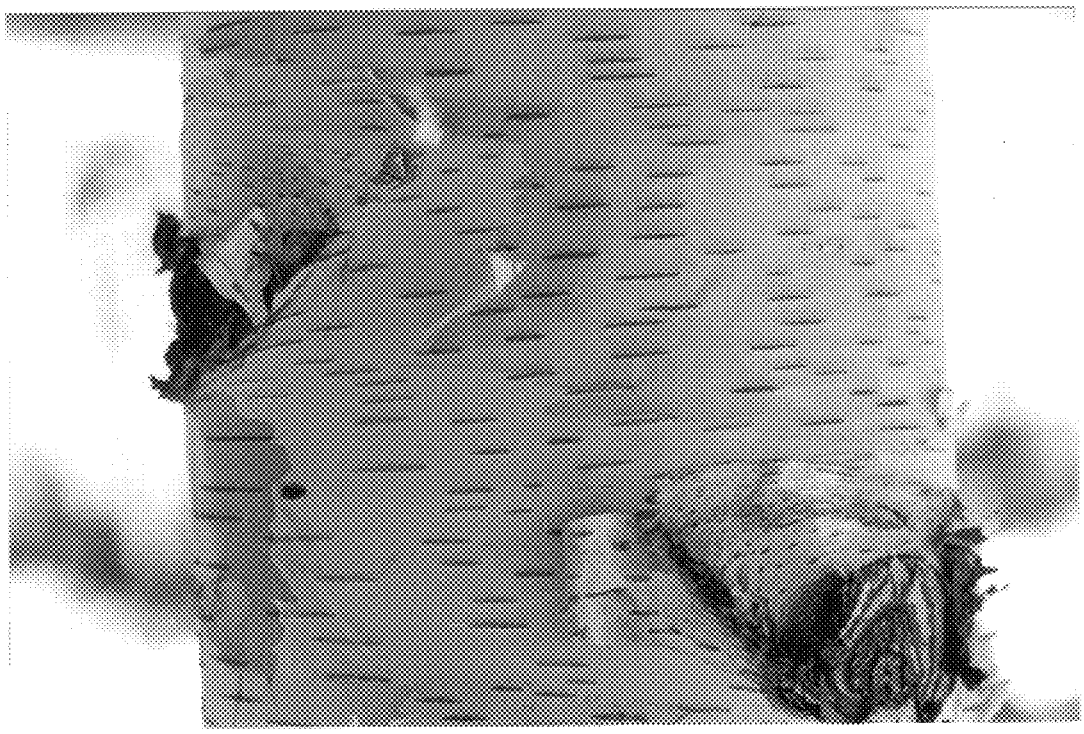
FIG. 3 shows the semi-exfoliating bark.
Figure 4:
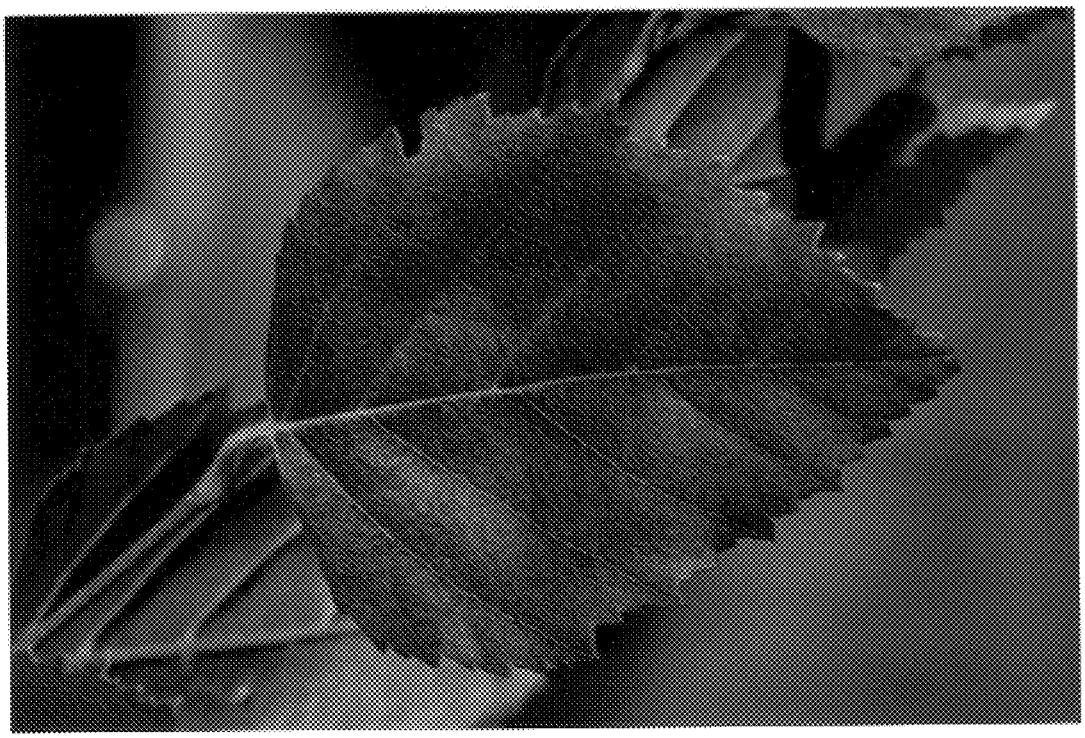
FIG. 4 shows a close-up of the upper side of a leaf.
Figure 5:
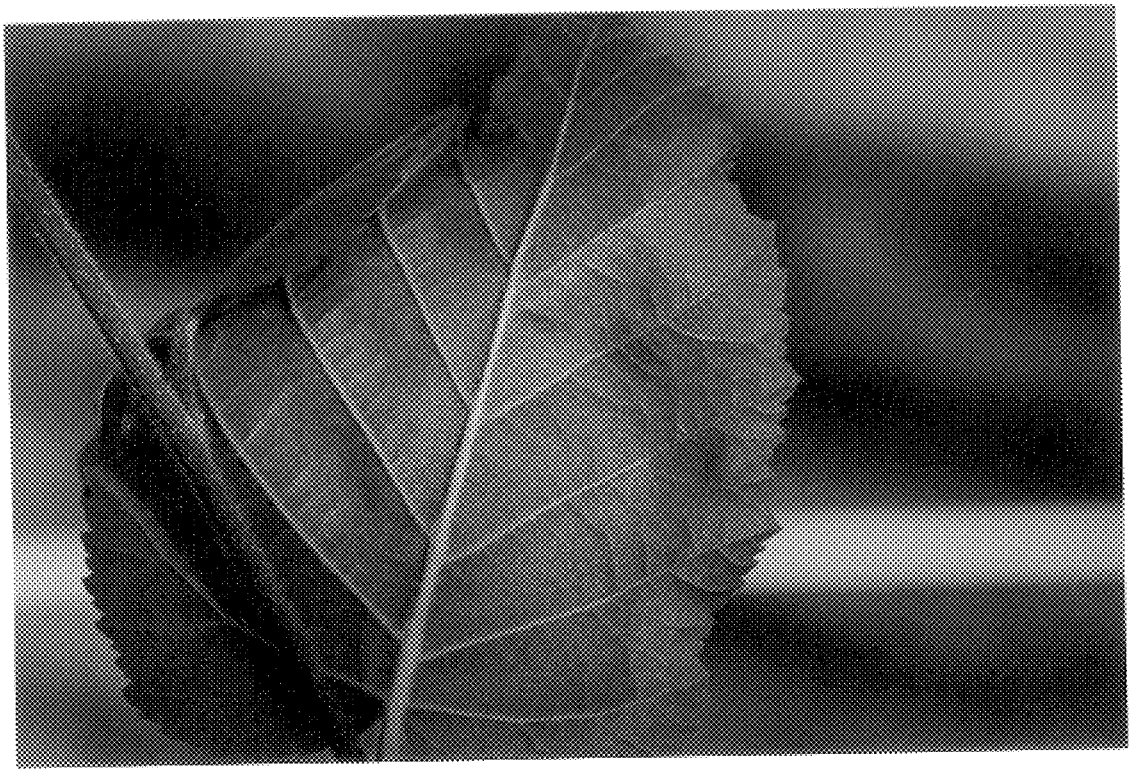
FIG. 5 shows a close-up of the under side of a leaf.

In the following description, color references are made to The Royal Horticultural Society (R.H.S.) Colour Chart. The color values were determined in natural light in August 1999 in Sturgeon Bay, Wis.

Classification:

*Botanical.*—*Betula papyrifera* 'Uenci'.

Parentage:

*Origin.*—Found as seedling in a group of *Betula papyrifera* in a provenance test plot in Wooster, Ohio in 1986.

*Parentage.*—Seed parent: *Betula papyrifera.* Pollen parent: *Betula papyrifera.*

Tree:

*Trunk.*—Multiple stem: Single-trunked tree. Size: Diameter at age 10 is approximately 11.5 cm at 1.2 m above the ground. Bark at maturity: White, close to (R.H.S. 155C) semi-exfoliating to greyed-orange bark (RHS 165C).

*Branches.*—Angle of attachment: 50°. Spacing: Between whorls 40–50 cm. Size: 3–4 cm when tree is 2.4 m. Bark: Color changes with age: at 4 years, brown (RHS 200C) turning to white close to RHS (155D) with semi-exfoliation, exposing greyed-orange bark RHS 165C. Lenticels: Small, but numerous, size: 2–4 mm×1–2 mm. Color: RHS greyed-oranged 165A.

*Height.*—8.8 m at about 10 years of age.

*Growth habit or form.*—Narrow, open growth habit, upright; Growth rate: fast, about 0.8–2.0 m per year, depending on summer temperature, fertility and water availability.

*Foliage.*—Size of leaf: Length: with petiole 7–10 cm, without petiole 5–10 cm; Width: 3–7 cm; Arrangement: alternate; Shape of leaf: serrate, rounded base, ovate to deltoid with acute apex acuminate apices and double serrate margins; Texture: Smooth; Ribs and veins: mid-rib with 12 veins sub opposite (RHS 144D). Pubescence distribution: on under side of mid rib and in axils of veins; Quantity: Singles with some 2 per spur, approximately 20 leaves/50 cm of stem. Color: upper side, dark green (RHS 147A), under side dark green (RHS 147B). Petiole: Length: 1.5–3 cm. Diameter: 1.5–2.0 mm; Color: RHS 162-C.

*Pest resistance.*—High resistance to Bronze Birch Borer as distinguished with other trees in an area of heavy Bronze Birch Borer infestation in Wooster, Ohio and Sturgeon Bay, Wis. Highly resistant to Leafhoppers.

*Disease and pest susceptibility.*—Moderately susceptible to leafminor.

*Winter hardiness/drought/heat resistance.*—Winter hardiness in Zone 3 and good drought/heat resistance in Zone 7.

*Flowers.*—None have been observed to date.

*Reproductive organs.*—Typical of the species.

What is claimed is:

1. A new and distinct cultivar of birch tree named 'Uenci' as illustrated and described.

* * * * *